United States Patent
Chadwick et al.

(10) Patent No.: US 8,011,239 B1
(45) Date of Patent: Sep. 6, 2011

(54) IN SITU SEDIMENT ECOTOXICITY ASSESSMENT SYSTEM

(75) Inventors: David B. Chadwick, San Diego, CA (US); Gunther H. Rosen, San Diego, CA (US); G. Allen Burton, Ann Arbor, MI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 196 days.

(21) Appl. No.: 12/615,919

(22) Filed: Nov. 10, 2009

(51) Int. Cl.
*E21C 39/00* (2006.01)
(52) U.S. Cl. .................... 73/170.32; 210/785
(58) Field of Classification Search ............... None
See application file for complete search history.

(56) References Cited

U.S. PATENT DOCUMENTS

| | | | |
|---|---|---|---|
| 3,975,957 A | 8/1976 | Mesecar | |
| 5,635,393 A * | 6/1997 | Bhatnagar et al. | 435/262.5 |
| 5,877,398 A * | 3/1999 | Candido et al. | 800/13 |
| 6,823,749 B1 | 11/2004 | Welsh et al. | |
| 7,222,546 B2 | 5/2007 | St. Germain | |
| 2005/0254899 A1* | 11/2005 | Tyler | 405/15 |
| 2007/0122870 A1* | 5/2007 | Turley et al. | 435/34 |
| 2007/0253785 A1* | 11/2007 | Tyler | 405/302.6 |
| 2008/0016759 A1* | 1/2008 | Tyler | 47/31 |
| 2009/0045149 A1* | 2/2009 | Murray et al. | 210/785 |

OTHER PUBLICATIONS

Anderson BS et al, "A Comparison of In-situ and Laboratory Toxicity Tests With the Estuarine Amphipod Eohaustorius estuarius", Archives of Environmental Contamination and Toxicology, 2004, pp. 52-60, vol. 46, Springer-Verlag, New York, USA.

Anderson BS et al, "Influence of Sample Manipulation on Contaminant Flux and Toxicity at the Sediment-Water Interface", Marine Environmental Research, 2001, pp. 191-211, vol. 51, Elsevier Science Ltd.

Burton Jr., G. Allen et al., "In-situ Exposures Using Caged Organisms: A multi-compartment approach to detect aquatic toxicity and bioaccumulation", Environmental Pollution, 2005, pp. 133-144, vol. 134, Elsevier Science Ltd.

Moreira SM, et al., "A Short-term Sub-lethal In-situ Toxicity Assay With Hediste diversicolor (Polychaeta) for Estuarine Sediments Based on Post-exposure Feeding", Environmental Toxicology and Chemistry, 2005, pp. 2010-2018, vol. 24, Setac Press, USA.

(Continued)

*Primary Examiner* — Andre Allen
(74) *Attorney, Agent, or Firm* — Ryan J. Friedl; Kyle Eppele

(57) ABSTRACT

A system includes a plurality of chamber holders having openings therein, and an exposure chamber positioned in each chamber holder. Each exposure chamber includes a mesh portion and a top end cap. One exposure chamber contains a mesh bottom and one contains a closed bottom. Each chamber holder is positioned within an opening contained within a base portion. One exposure chamber may extend beyond the lower boundary of the base portion. A top portion may be secured to the base portion to contain the chamber holders. A pump, with connected supply hose, may be coupled to the top portion. The supply hose is routed through the chamber holders such that a supply hose opening is adjacent to each chamber holder. The system may include a water quality sensor and a passive sampling device coupled to the base portion. A deployment system may be connected to the top portion.

20 Claims, 7 Drawing Sheets

OTHER PUBLICATIONS

Ringwood AH, et al., "Comparative In-situ and Laboratory Sediment Bioassays With Juvenile Mercenaria Mercenaria", Environmental Toxicology and Chemistry, 2002, pp. 1651-1657, vol. 21, No. 8, Setac Press, USA.

Wharfe J, et al., "In-situ Methods of Measurement—An Important Line of Evidence in the Environmental Risk Framework", Integrated Environmental Assessment and Management, 2007, pp. 268-274, vol. 3, No. 2, Setac Press, USA.

* cited by examiner

US 8,011,239 B1

IN SITU SEDIMENT ECOTOXICITY ASSESSMENT SYSTEM

FEDERALLY SPONSORED RESEARCH AND DEVELOPMENT

The In Situ Sediment Ecotoxicity Assessment System is assigned to the United States Government and is available for licensing for commercial purposes. Licensing and technical inquiries may be directed to the Office of Research and Technical Applications, Space and Naval Warfare Systems Center, Pacific, Code 2112, San Diego, Calif., 92152; voice (619) 553-2778; email ssc_pac_T2@navy.mil. Reference Navy Case No. 99948.

BACKGROUND

The last several years have seen an increase in the number of occurrences of contamination of aquatic systems with harmful bacteria and/or toxic substances. When such contaminations occur, it is paramount that the effects of such contamination be studied. One method of characterizing the exposure and effects of aquatic system contamination is by sampling sediment in a contaminated region and then performing tests on the sediment in a laboratory environment. This process typically involves taking multiple sediment samples from a particular location at specific time intervals, removing the samples from the sampling location, and adding the sediment samples to beakers or aquaria in a laboratory at a later time period. Test organisms are then added and tests are conducted for a specific time period under strictly controlled laboratory conditions using standardized toxicity testing protocols. The above sediment contamination assessment approach is well established, but does not sufficiently represent the true exposure effects to aquatic communities, particularly when the source of contamination is ephemeral or the exposure varies over time and with ambient conditions.

Alteration of exposure due to sampling and manipulation of samples in preparation for laboratory testing is problematic. Sediment sample manipulation removes the natural stratification that affects exposure to test organisms and also may result in degradation, volatilization, or other alterations of contaminants that occur with exposure to air. When samples are removed from the field, they undergo a variety of physical and chemical changes, which may alter the bioavailability and toxicity of any contaminants they possess. Such alteration may possibly result in false conclusions. Further, laboratory tests may overestimate toxicity due to increasingly higher concentrations of toxicants in the static overlying water, as toxicants desorb from the sediment. Thus, results from laboratory exposures are not necessarily indicative of what is encountered by natural populations in the field.

Additionally, various water quality characteristics unique to each field site also affect the availability of contaminants for uptake by organisms and potential for biological effects (e.g. toxicity). Such water quality characteristics are removed or changed by conducting testing in a laboratory. However, even when the testing is conducted in situ, these water quality characteristics are typically measured either on discrete samples (non-continuous monitoring), or the sensors are placed adjacent to the test chambers themselves, resulting in measurements that may be different from conditions encountered by the test organisms.

A need exists for an improved system for assessing the true exposure and effects of a toxic contaminant on an aquatic environment.

DETAILED DESCRIPTION OF SOME EMBODIMENTS

Figure 1:
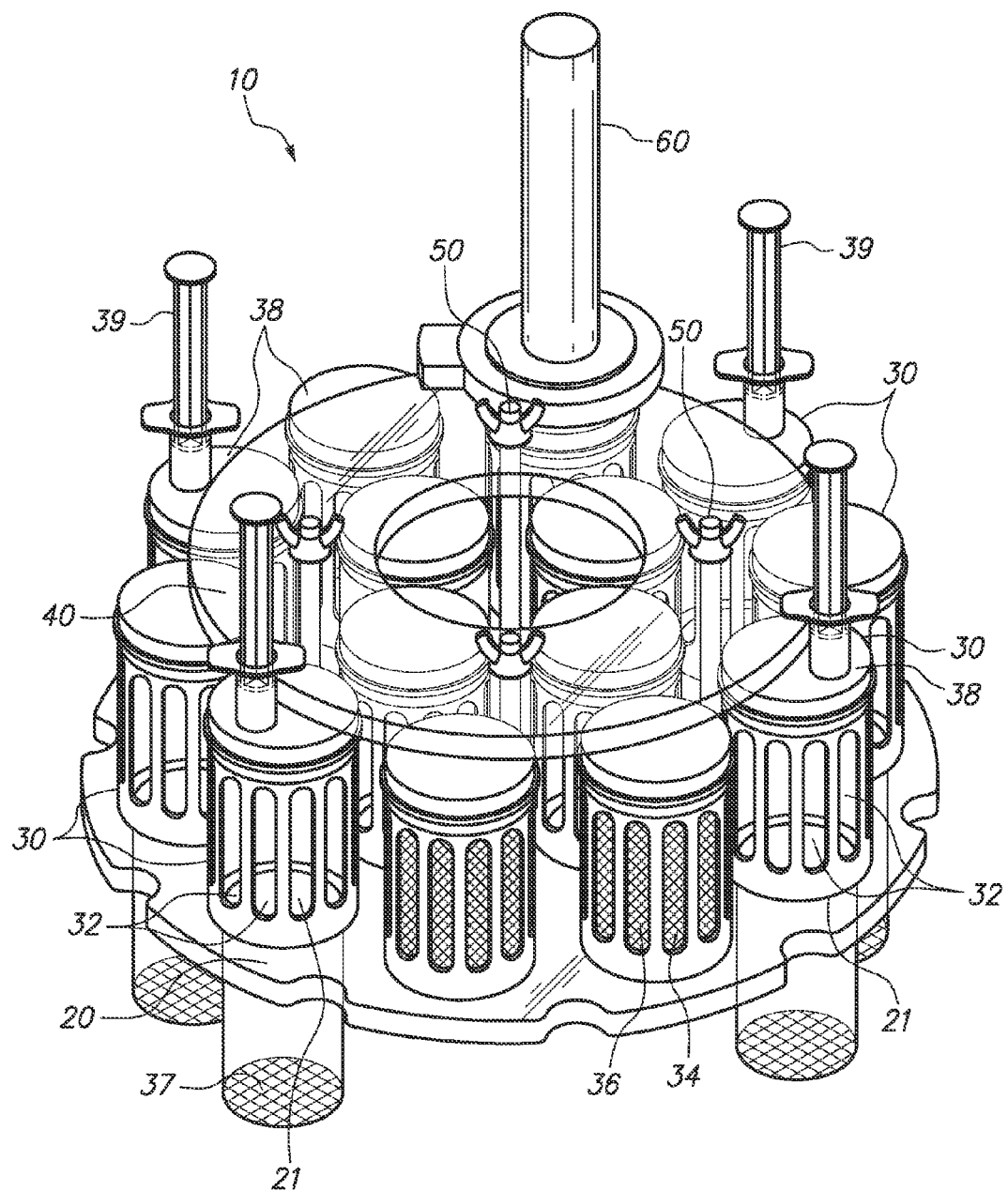
FIG. 1 shows a top perspective view of an embodiment of a system in accordance with the In Situ Sediment Ecotoxicity Assessment System.

FIG. 1 shows a top perspective view of an embodiment of a system 10 in accordance with the In Situ Sediment Ecotoxicity Assessment System. System 10 may include a base portion 20, a plurality of cylindrical chamber holders 30, and a top portion 40. Base portion 20 may have a plurality of base portion openings 21, with each chamber holder 30 positioned within one of the base portion openings 21. Each chamber holder 30 includes a plurality of chamber holder openings 32. In some embodiments, chamber holder openings are vertically-oriented, as shown in FIG. 1.

Figure 2:
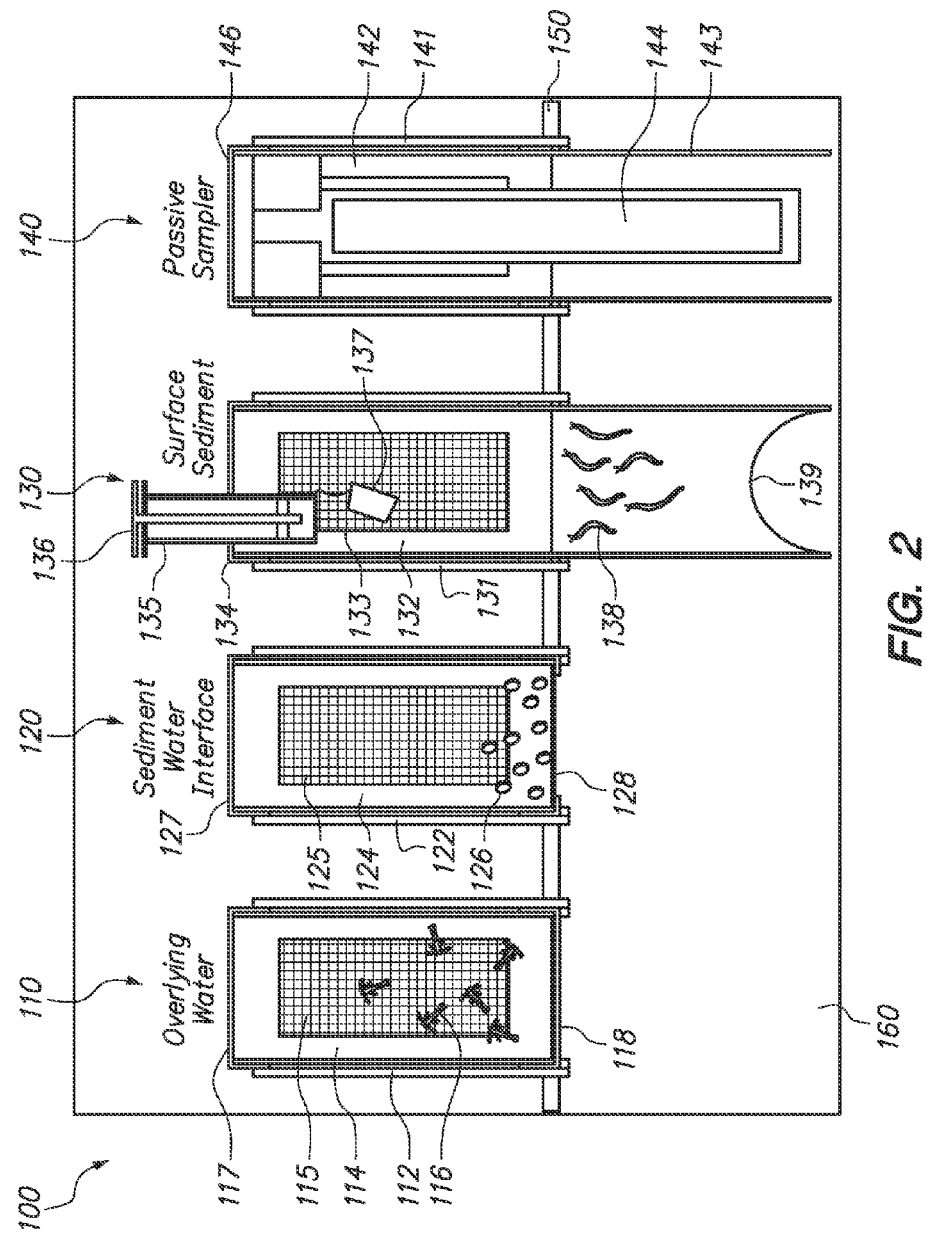
FIG. 2 shows a diagram of side views of embodiments of chamber holders and exposure chambers positioned near or in sediment, in accordance with the In Situ Sediment Ecotoxicity Assessment System.

System 10 further includes an exposure chamber 34 positioned in each chamber holder 30. Each exposure chamber 34 may include a mesh portion 36 and a top end cap 38. Some embodiments of the exposure chambers 34 contain a mesh bottom 37. A mesh bottom allows for sediment to enter into exposure chamber 34. Some embodiments of the exposure chambers 34 contain a closed bottom to prevent water, sediment, and/or test subjects from escaping exposure chamber 34. Some embodiments of exposure chambers 34 extend beyond the lower boundary of base portion 20, as shown in FIG. 1. When system 10 is placed in sediment, exposure chambers 34 extending beyond the lower boundary of base portion 20 will be embedded within the sediment (as shown in FIG. 2), allowing test subjects to be directly exposed to the sediment. In some embodiments, at least one exposure chamber 34 contains a syringe 39 embedded in top end cap 38, as discussed more in detail with respect to FIG. 2.

Top portion 40 is secured to base portion 20 such that chamber holders 30 are positioned between top portion 40 and base portion 20. In some embodiments, top portion 40 is secured to base portion 20 by a combination 50 of screws and wing nuts. Other methods for securing top portion 40 to base portion 20 may be used as recognized by one having ordinary skill in the art.

In some embodiments, system 10 may further include a water quality sensor 60, such as that manufactured commercially by the In Situ Corporation, coupled to base portion 20. As an example, water quality sensor 60 may be securely positioned within one of the exposure chambers 34 inside one of the base portion openings 21. Water quality sensor 60 allows for continuous measurements of pH, temperature, depth, salinity, conductivity, dissolved oxygen, ammonia, and other parameters, inside exposure chambers 34. As a result, water quality measurements will be indicative of conditions actually experienced by the test organisms, allowing for improved data interpretation.

In some embodiments, system 10 may further include a solid-phase micro-extraction (SPME) fiber holder (not shown) connected thereto. The SPME fiber holder may be a thin, cylindrical housing that contains a small glass fiber with a polymer coating that sorbs organic contaminants. The SPME fiber holder may be attached to system 10 by a stainless steel bracket welded to a nut that may be positioned at any specified sediment depth along one or more stainless rods that may extend from beneath base portion 20

As an example, base portion 20 is 18" in diameter and constructed from a polymer material, such as ½" thick acrylic, while top portion 40 is 13" in diameter and is comprised of a ½" thick acrylic ring. Base portion 20 may include a total of 14 base portion openings 21, with each opening having a 3⅛" diameter to accommodate cylindrical chamber holders 30. Chamber holders 30 may be permanently affixed to the platform, such as via glue, and may be comprised of ⅛" thick acrylic. Chamber holder openings 32 may be 3" long by ½" wide, allowing water flow to exposure chambers 34.

Exposure chambers 34 may be disposable, and may comprise cylindrical, clear plastic such as cellulose acetate butyrate, having a 1/16" thickness and an inner diameter of 2⅝". Each exposure chamber 34 may possesses two mesh cutouts, as shown in FIG. 2, to accommodate water flow. Each mesh cutout may be approximately 2¾" tall by 1¾" wide. The mesh pore size may be 250 µm, but may vary depending on the test type. The length of exposure chambers 34 may vary depending on the exposure type. As an example, an overlying water or sediment water interface exposure chamber 34 may be 5" long. Further, a surface sediment exposure chamber 34 may be 10" long and may extend beyond the lower boundary of base portion 20. Each exposure chamber 34 may have a cap affixed to the top of the exposure chamber to retain the chamber contents.

System 10 allows users to more accurately characterize biological exposure and effects at contaminated sediment sites by conducting controlled and integrated exposures with caged aquatic invertebrates, passive samplers, and water quality monitoring devices in the field using an integrated system instead of independently and on different time scales using traditional methods in a laboratory. The end result is more accurate assessments of ecological risk that can relate chemical exposure and biological effects.

FIG. 2 shows a diagram 100 of side views of embodiments of chamber holders and exposure chambers positioned in sediment 160. The chamber holders and exposure chambers shown in FIG. 2 may be used as any of the chamber holders 30 and exposure chambers 34 as contained within system 10. As shown, a first chamber holder 110 may be used to test overlying water conditions, a second chamber holder 120 may be used to test sediment/water interface conditions, a third chamber holder 130 may be used to test surface sediment, and a fourth chamber holder 140 may comprise a passive sampler. Chamber holders 110, 120, 130, and 140 may be secured to a base portion 150, with each of the chamber holders being securely affixed within a base portion opening.

Chamber holder 110 may include chamber holder wall 112 and an exposure chamber 114 disposed therein. Exposure chamber 114 may include at least one mesh portion 115. Mesh portion 115 serves to allow water to circulate within exposure chamber 114 to help alleviate stress on test subjects 116 contained within exposure chamber 114. The size of the holes of mesh portion 115 may vary depending upon the size of the test subjects contained within exposure chamber 114. Exposure chamber 114 also includes a top end cap 117 and closed bottom portion 118 secured thereto, to prevent test subjects 116 from escaping from exposure chamber 114. As an example, closed bottom portion 118 may comprise another end cap similar to top end cap 117, with top end cap 117 and closed bottom portion 118 being either screwed or press-fit to enclosure chamber 114.

Chamber holder 120 may include chamber holder wall 122 and an exposure chamber 124 disposed therein. Exposure chamber 124 may include at least one mesh portion 125 to allow water to circulate within exposure chamber 125 to help alleviate stress on test subjects 126 contained within exposure chamber 124. Exposure chamber 124 also includes a top end cap 127 and mesh bottom portion 128 secured thereto, to prevent test subjects 126 from escaping from exposure chamber 124. Mesh bottom portion 128 serves to expose test subjects 126 to sediment, enabling test subjects 126 to be exposed to the effects of the sediment/water interface.

Chamber holder 130 may include chamber holder wall 131 and an exposure chamber 132 disposed therein. Exposure chamber 132 may include at least one mesh portion 133 to allow water to circulate within exposure chamber 132 to help alleviate stress on test subjects 138 contained within exposure chamber 132. Exposure chamber 132 extends beyond the lower boundary of base portion 150 into sediment 160. The amount of distance exposure chamber 132 extends into sediment 160 may vary. As an example, exposure chamber 132 may extend 5" beyond the lower boundary of base portion 150. Exposure chamber 132 also includes a top end cap 134 to prevent test subjects 138 from escaping exposure chamber 132.

Exposure chamber 132 may further include a modified end cap 139 that is sliced to allow sediment and test subjects to be retained within exposure chamber 132 when it is extracted from the water. In some embodiments, modified end cap 139 may be circular and may be sliced into eight segments, similar to slicing a pie. Modified end cap 139 is attached to exposure chamber 132 and an acrylic ring (not shown) approximately 2½" in diameter may be used to hold modified end cap 139 open during deployment by pushing the eight end cap segments up into exposure chamber 132. When exposure chamber 132 is pushed into sediment 160, the acrylic ring is pushed up into exposure chamber 132, allowing modified end cap 139 to close when retrieved at the end of the exposure.

Exposure chamber 132 may also contain a modified plastic syringe 135 embedded into top end cap 134. Syringe 135 holds test subjects that are deployed into exposure chamber 132 following placement of base portion 150 on sediment 160. The modified syringe contains a silicone stopper 137 attached to a piece of monofilament. A plastic screw attached to the syringe plunger 136 pushes out silicone stopper 137, releasing test subjects 138 into exposure chamber 132.

Chamber holder 140 may include chamber holder wall 141 and an exposure chamber 142 disposed therein. A portion 143 of exposure chamber 142 extends beyond the lower boundary of base portion 150 into sediment 160. The amount of distance exposure chamber 142 extends into sediment 160 may vary. As an example, exposure chamber 142 may extend 5" beyond the lower boundary of base portion 150. Exposure chamber 142 also includes a top end cap 146. Exposure chamber 142 may further includes a passive sampling device 144 that serves to measure non-polar organic chemicals or metals in both the overlying water and sediment. An example of a passive sampling device 144 is a DGT (diffusion gradient in thin films) that may be obtained commercially from DGT Research Ltd, Lancaster, UK.

Figure 3:
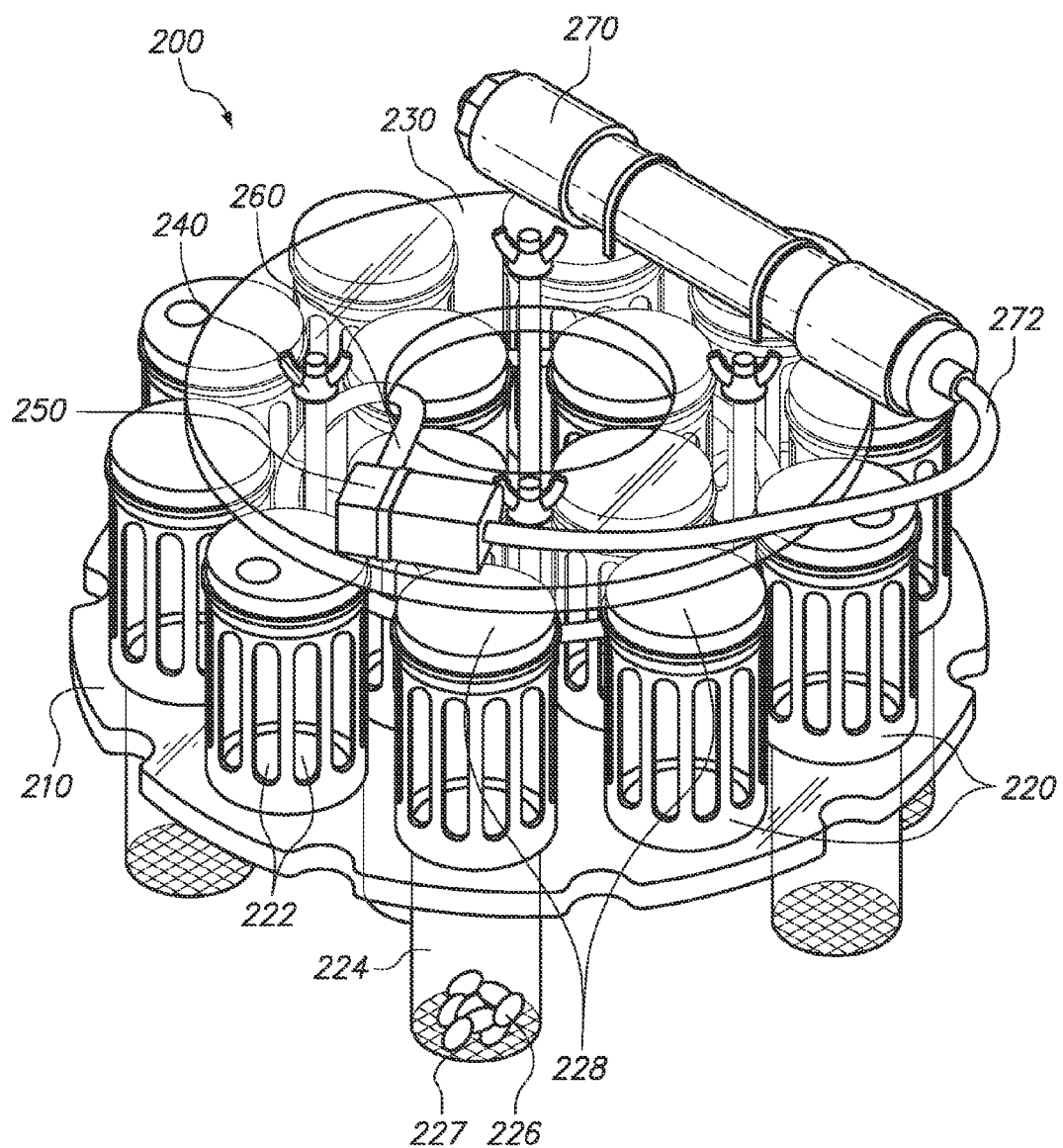
FIG. 3 shows a top perspective view of an embodiment of a system including a circulating pump in accordance with the In Situ Sediment Ecotoxicity Assessment System.
Figure 4:
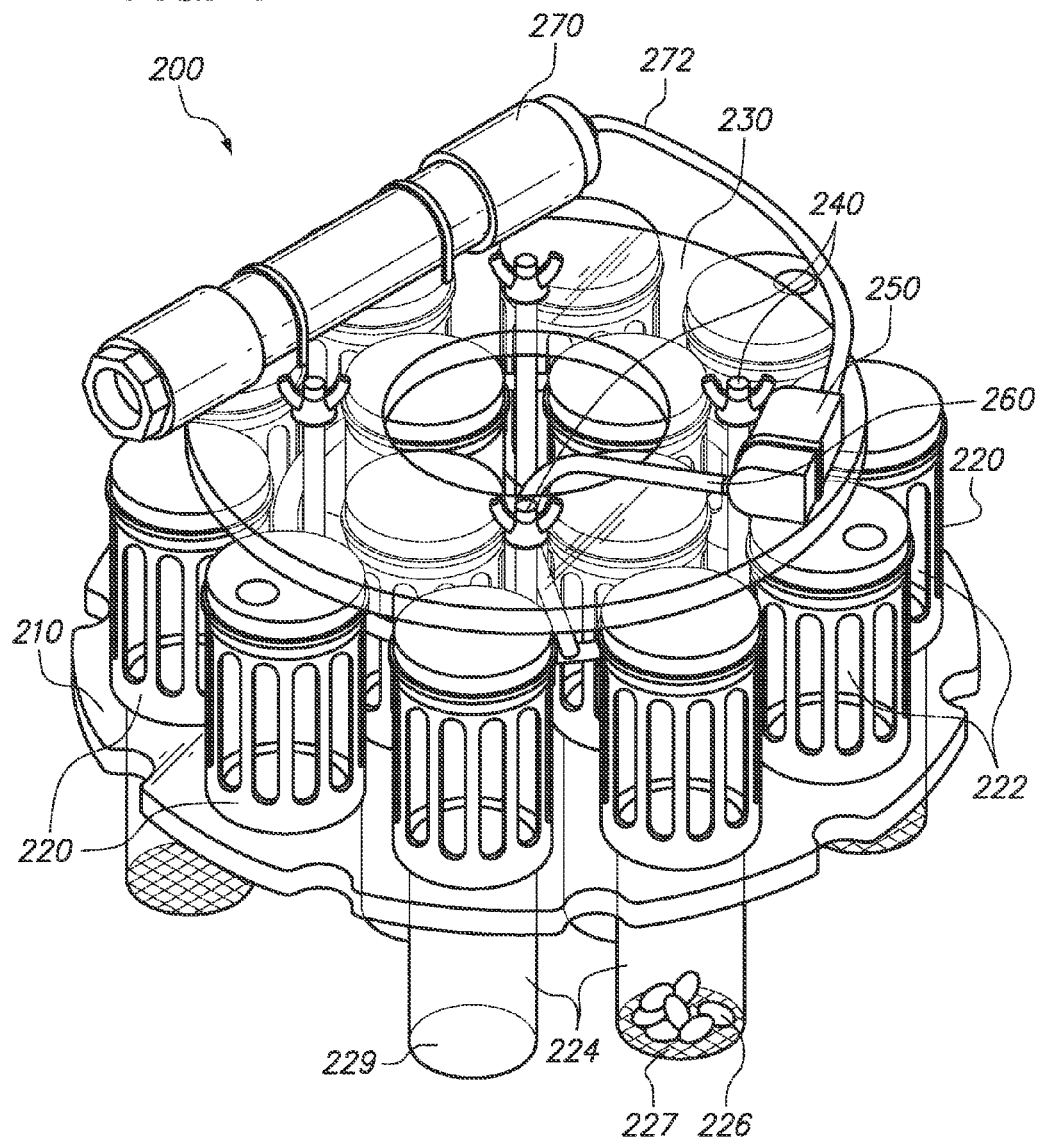
FIG. 4 shows a side view of the system shown in FIG. 3.
Figure 5:
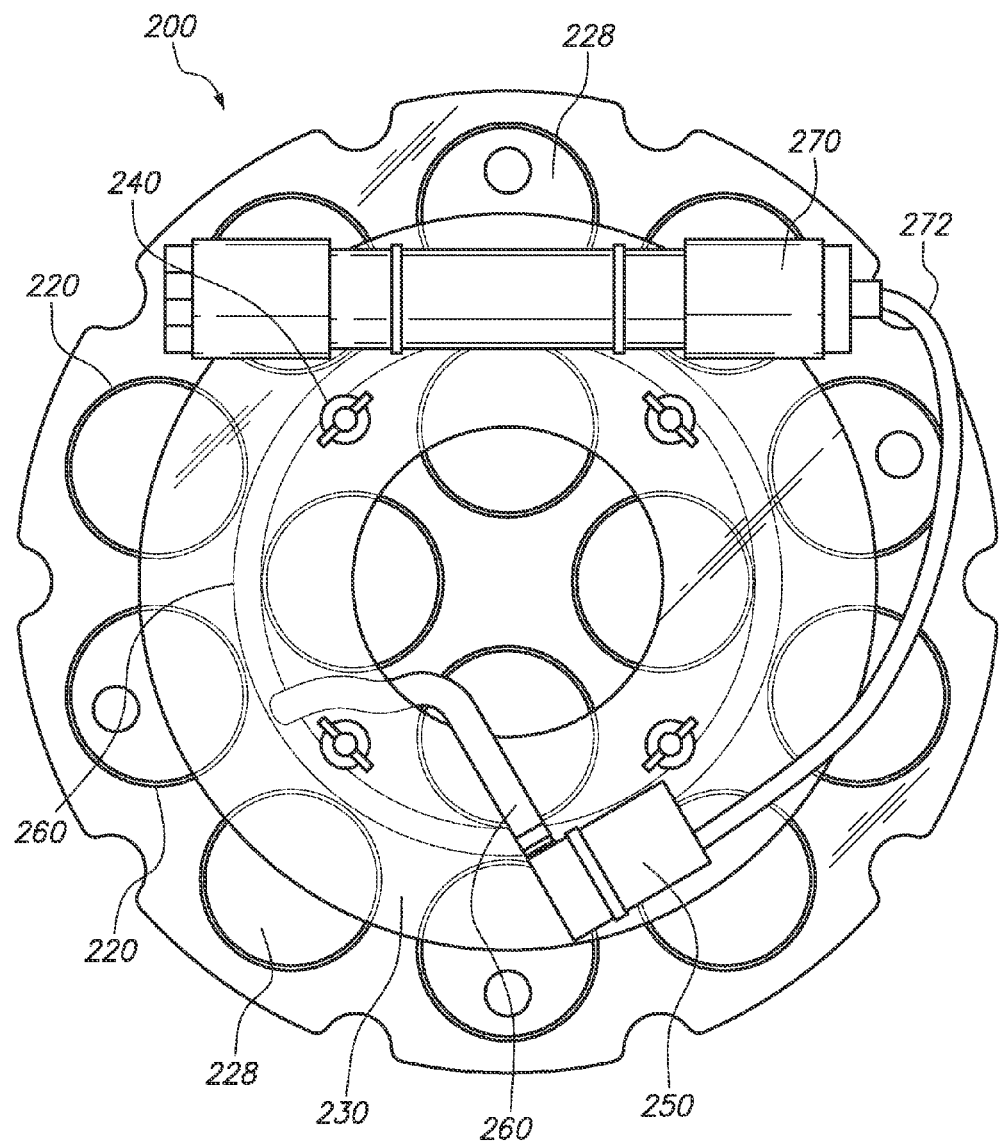
FIG. 5 shows a top view of the system shown in FIG. 3.

Referring to FIGS. 3-5, FIG. 3 shows a top perspective view, FIG. 4 shows a side view, and FIG. 5 shows a top view of an embodiment of a system 200 in accordance with the In Situ Sediment Ecotoxicity Assessment System. Components of system 200 having the same name as components of system 10 may be configured the same as or similar to those components of system 10. System 200 may include a base portion 210, a plurality of chamber holders 220, and a top portion 230. Base portion 210 may have a plurality of base portion openings, with each chamber holder 220 positioned within one of the base portion openings. Each chamber holder 220 includes a plurality of chamber holder openings 222.

System 200 may further include an exposure chamber 224 positioned in each chamber holder 220. Exposure chambers 224 may be similar to those shown in FIG. 2, and may contain test subjects 226. For example, an exposure chamber 224 may contain a mesh cutout portion (such as mesh portion 133 of FIG. 2), a mesh bottom portion 227 or a closed bottom portion 229 (see FIG. 4), and a top end cap 228. Top portion 230 is secured to base portion 210 such that chamber holders 220 are positioned between top portion 230 and base portion 210. In some embodiments, top portion 230 is secured to base portion 210 by a combination 240 of screws and wing nuts. In some embodiments, system 200 may further include a water quality sensor (such as water quality sensor 60 of FIG. 1) coupled to base portion 210.

System 200 further includes a re-circulating pump 250 attached to top portion 230. Pump 250 may be attached by fasteners, straps, screws, or other attachment means as recognized by one having ordinary skill in the art. A power source 270, such as an enclosed battery pack, may be attached to top portion 230 to supply power to pump 250 via cord 272 (see FIG. 5). A supply hose 260 is connected to pump 250. Supply hose 260 contains a plurality of supply hose openings (not shown) therein. As shown in FIG. 5, supply hose 260 is routed through chamber holders 220 such that a supply hose opening is adjacent to each chamber holder 220. Such a configuration allows water to be pumped into supply hose 260 and distributed through the supply hose openings to each chamber holder 220, and hence each exposure chamber. The supply of additional water flow to the exposure chambers helps maintain acceptable water quality in oxygen poor environments.

Figure 6:
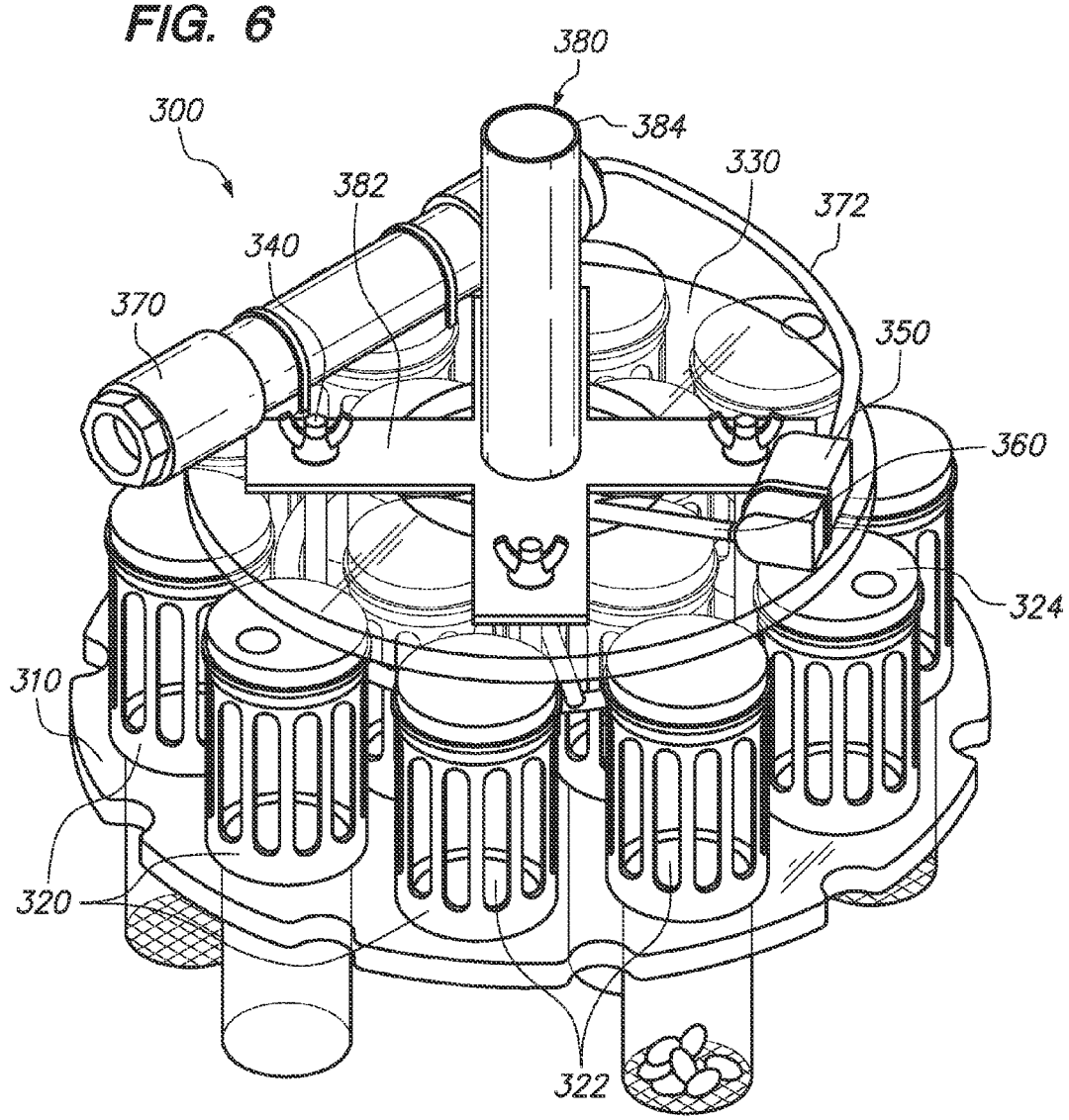
FIG. 6 shows a top perspective view of an embodiment of a system including a deployment mechanism in accordance with the In Situ Sediment Ecotoxicity Assessment System.
Figure 7:
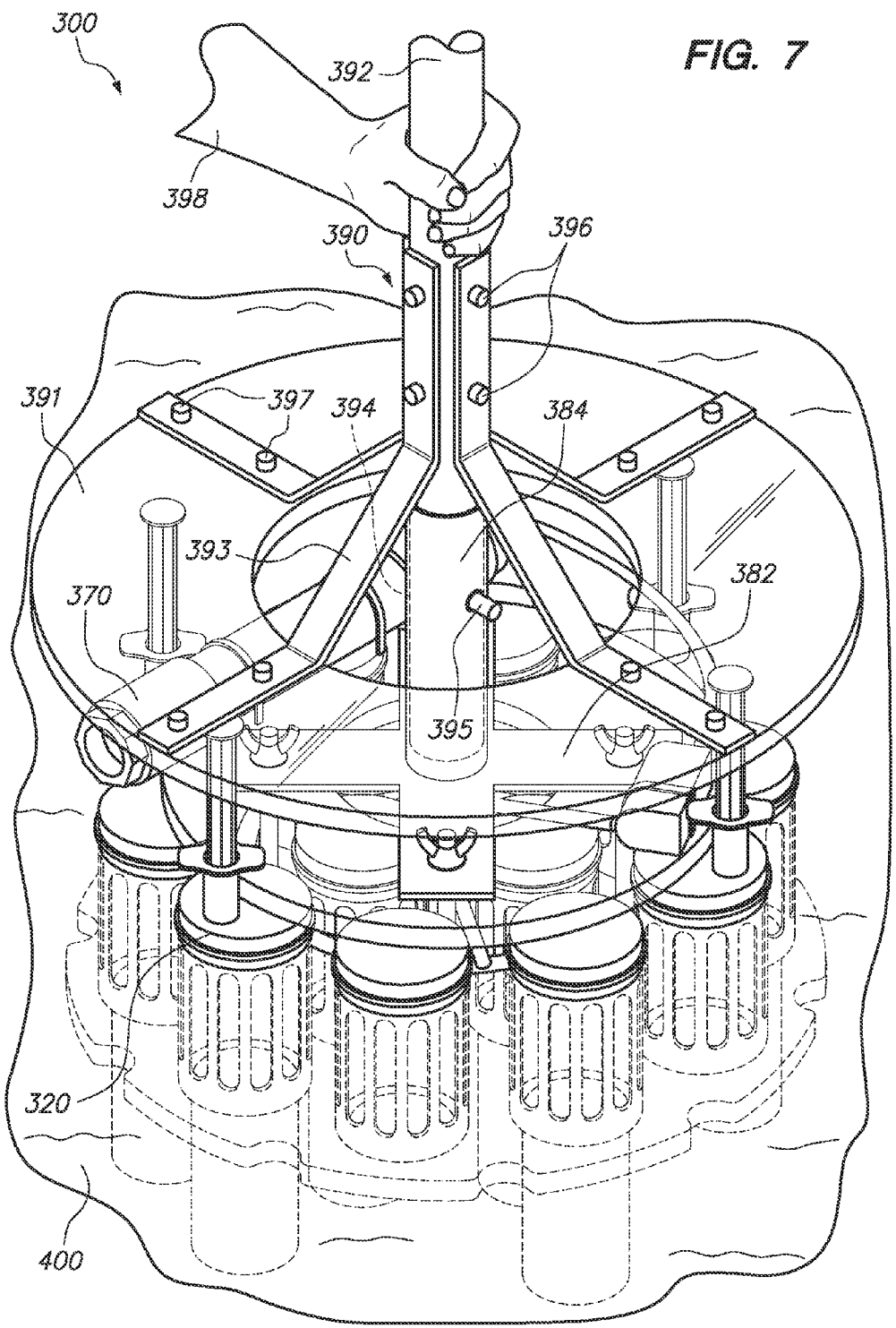
FIG. 7 shows a top perspective view of a system including a deployment mechanism being deployed in a body of water.

Referring to FIGS. 6 and 7, FIG. 6 shows a top perspective view of the bottom portion of an embodiment of a system 300 in accordance with the In Situ Sediment Ecotoxicity Assessment System, while FIG. 7 shows a top perspective view of a top portion of system 300 deployed in a body of water. System 300 may be configured similarly to system 200, including a base portion 310, a plurality of chamber holders 320 having chamber holder openings 322 therein, exposure chambers having top end caps 324, a top portion 330, a pump 350, a supply hose 360, and a power source 370. As an example, top portion 330 may be secured to base portion 310 by combination 340 of screws and wing nuts.

System 300 may further comprise a deployment system coupled to top portion 330. The deployment system allows for system 300 to be deployed in a body of water without the need of a diver. The deployment system may include a deployment system attachment portion 380 coupled to top portion 330. Deployment system attachment portion 380 includes attachment securing members 382 and pole attachment portion 384 coupled thereto. As an example, pole attachment portion 384 may be welded to securing members 382. Deployment system attachment securing members 382 may be secured to top portion 330 via screw and nut combination 340.

The deployment system may further include a deployment system top portion 390 (see FIG. 7) coupled to deployment system attachment portion 380. Deployment system top portion 390 may include a support portion 391, a deployment system pole 392 coupled to support portion 391 by a plurality of securing members 393. The end 394 of the deployment system pole 392 proximate to support portion 391 is configured to be inserted into the deployment system pole attachment portion 384. The deployment system may further include a connector 395, such as a pin, for securing deployment system pole 392 to deployment system attachment portion 384. In embodiments where connector 395 is a pin, the pin may be slide through openings (not shown) in both deployment system attachment portion 384 and end 394 of deployment system pole. Securing members 393 may be connected to deployment system pole 392 via screws 396 and to support portion 391 via screws 397.

In operation, a user 398 deploys system 300 in a body of water 400, which may be a freshwater or salt water environment. System 300 may be deployed in both shallow water and deep water. User 398 may then insert end 394 of deployment system pole 392 into deployment system pole attachment portion 384 and secure it thereto by use of connector 395. In embodiments of system 300 wherein one or more exposure chamber top end caps 324 contain a modified syringe therein, when user 398 inserts end 394 into deployment system pole attachment portion 384, the support portion 391 presses down upon the syringe plunger such that the syringe plunger pushes out the silicone stopper to release the test subjects into the exposure chamber. System 300 may then be left to reside within the body of water for a predetermined time period to allow the test subjects to be exposed to the environment.

Advantages of using systems such as system 10, 200, and 300 over traditional laboratory-based approaches include 1) increased realism; 2) reduced sample manipulation; 3) integration of multiple stressors, both natural and man-made; 4) the ability to incorporate spatial and temporal variability; 5) the ability to assess risk in specific matrices; and 6) the ability to integrate exposure with effects based measurements. The realism is increased by exposing organisms to conditions much closer to those that represent conditions natural populations will encounter. By reducing sample manipulation, contaminant stratification is not sacrificed and redox gradients do not change, thereby resulting in less chance for alteration of bioavailability and toxicity as compared to laboratory testing on grab samples.

Stressors that might be critical in appropriate evaluation of risk at the site, such as those associated with ground water upwelling, which can vary over time (e.g. with the tides), are also more likely to be incorporated into the assessment in continuous in situ exposures. Volatile contaminants that might be lost during manipulation will also be integrated into properly conducted in situ exposures. Conducting the testing in situ reduces the likelihood for physical-chemical changes that sediments undergo when removed, homogenized, and stored in the laboratory.

Many modifications and variations of the In Situ Sediment Ecotoxicity Assessment System are possible in light of the above description. Within the scope of the appended claims, the In Situ Sediment Ecotoxicity Assessment System may be practiced otherwise than as specifically described. Further, the scope of the claims is not limited to the implementations and embodiments disclosed herein, but extends to other implementations and embodiments as may be contemplated by those having ordinary skill in the art.

We claim:

1. A system comprising:
   a plurality of chamber holders, each chamber holder containing a plurality of chamber holder openings; and
   an exposure chamber positioned in each of the chamber holders, each exposure chamber comprising a mesh portion and a top end cap, wherein at least one of the exposure chambers contains a mesh bottom and at least one of the exposure chambers contains a closed bottom.

2. The system of claim 1 further comprising a base portion having a plurality of base portion openings, wherein each chamber holder is positioned within one of the base portion openings.

3. The system of claim 2, wherein the chamber holders are cylindrical in shape and are permanently coupled to the base portion.

4. The system of claim 2, wherein at least one of the exposure chambers extends beyond the lower boundary of the base portion.

5. The system of claim 2 further comprising a top portion secured to the base portion such that the chamber holders are positioned between the top portion and the base portion.

6. The system of claim 5, wherein the base portion is substantially circular in shape and the top portion is ring-shaped.

7. The system of claim 5, wherein the base portion, the top portion, and the chamber holders are comprised of a polymer material.

8. The system of claim 5, further comprising:
   a pump attached to the top portion; and
   a supply hose connected to the pump, the supply hose having a plurality of supply hose openings therein, wherein the supply hose is routed through the chamber holders such that a supply hose opening is adjacent to each chamber holder.

9. The system of claim 5, further comprising a deployment system, coupled to the top portion, comprising:
   a deployment system attachment portion coupled to the top portion, the deployment system attachment portion including
      more than one attachment securing members, and
      a deployment system pole attachment portion coupled to the attachment securing members;
   a deployment system top portion coupled to the deployment system attachment portion, the deployment system top portion including
      a support portion,
      a deployment system pole coupled to the support portion by a plurality of securing members, wherein the end of the deployment system pole proximate to the support portion is configured to be inserted into the deployment system pole attachment portion, and
      a connector for securing the deployment system pole to the deployment system attachment portion.

10. The system of claim 2, further comprising a water quality sensor coupled to the base portion.

11. The system of claim 2 further comprising a passive sampling device coupled to the base portion.

12. The system of claim 1, wherein at least one exposure chamber contains a syringe embedded in the top cap, the syringe having a silicone stopper coupled thereto.

13. A system comprising:
   a base portion having a plurality of base portion openings;
   a plurality of cylindrical chamber holders, each chamber holder positioned within one of the base portion openings, each chamber holder containing a plurality of vertically-oriented chamber holder openings;
   an exposure chamber positioned in each of the chamber holders, each exposure chamber comprising a mesh portion and a top end cap, wherein at least one of the exposure chambers contains a mesh bottom, at least one of the exposure chambers contains a closed bottom, and at least one of the exposure chambers extends beyond the lower boundary of the base portion; and
   a top portion secured to the base portion such that the chamber holders are positioned between the top portion and the base portion.

14. The system of claim 13, wherein the base portion is substantially circular in shape and the top portion is ring-shaped, and wherein the base portion, the top portion, and the chamber holders are comprised of a polymer material.

15. The system of claim 13, further comprising:
   a pump attached to the top portion; and
   a supply hose connected to the pump, the supply hose having a plurality of supply hose openings therein, wherein the supply hose is routed through the chamber holders such that a supply hose opening is adjacent to each chamber holder.

16. The system of claim 13, further comprising a deployment system, coupled to the top portion, comprising:
   a deployment system attachment portion coupled to the top portion, the deployment system attachment portion including
      more than one attachment securing members, and
      a deployment system pole attachment portion coupled to the attachment securing members;
   a deployment system top portion coupled to the deployment system attachment portion, the deployment system top portion including
      a support portion,
      a deployment system pole coupled to the support portion by a plurality of securing members, wherein the end of the deployment system pole proximate to the support portion is configured to be inserted into the deployment system pole attachment portion, and
      a connector for securing the deployment system pole to the deployment system attachment portion.

17. The system of claim 13, further comprising:
   a water quality sensor coupled to the base portion; and
   a passive sampling device coupled to the base portion.

18. A system comprising:
   a base portion having a plurality of base portion openings;
   a plurality of chamber holders, each chamber holder positioned within one of the base portion openings, each chamber holder containing a plurality of chamber holder openings;
   an exposure chamber positioned in each of the chamber holders, each exposure chamber comprising a mesh portion and a top end cap, wherein at least one of the exposure chambers contains a mesh bottom, at least one of the exposure chambers contains a closed bottom, and at least one of the exposure chambers extends beyond the lower boundary of the base portion;
   a top portion secured to the base portion such that the chamber holders are positioned between the top portion and the base portion;
   a pump attached to the top portion;
   a supply hose connected to the pump, the supply hose having a plurality of hose openings therein, wherein the supply hose is routed through the chamber holders such that a supply hose opening is adjacent to each chamber holder; and
   a water quality sensor coupled to the base portion.

19. The system of claim 18, further comprising a passive sampling device coupled to the base portion.

20. The system of claim 18, further comprising a deployment system, coupled to the top portion, comprising:
- a deployment system attachment portion coupled to the top portion, the deployment system attachment portion including
  - more than one attachment securing members, and
  - a deployment system pole attachment portion coupled to the attachment securing members;
- a deployment system top portion coupled to the deployment system attachment portion, the deployment system top portion including
  - a support portion,
  - a deployment system pole coupled to the support portion by a plurality of securing members, wherein the end of the deployment system pole proximate to the support portion is configured to be inserted into the deployment system pole attachment portion, and
- a connector for securing the deployment system pole to the deployment system attachment portion.

* * * * *